(12) United States Patent
Radeztsky

(10) Patent No.: US 6,326,979 B1
(45) Date of Patent: Dec. 4, 2001

(54) SYSTEM FOR AND METHOD OF CALIBRATING A COMPUTER MONITOR

(75) Inventor: John H. Radeztsky, Milwaukee, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/233,702

(22) Filed: Jan. 19, 1999

Related U.S. Application Data

(60) Provisional application No. 60/072,248, filed on Jan. 23, 1998.

(51) Int. Cl.[7] .................................................. G09G 5/00
(52) U.S. Cl. ............................ 345/660; 345/472; 345/681
(58) Field of Search .................................... 345/127, 131, 345/132, 173, 433, 438, 439, 660, 655, 666, 656, 681, 472, 472.1, 472.2; 382/117

(56) References Cited

U.S. PATENT DOCUMENTS

| | | | |
|---|---|---|---|
| 5,176,689 | * | 1/1993 | Hardy et al. .......................... 606/130 |
| 5,874,937 | * | 2/2000 | Kesatoshi ............................. 345/127 |
| 5,933,134 | * | 8/1999 | Shich ................................... 345/173 |
| 6,018,332 | * | 1/2000 | Nason et al. ......................... 345/127 |
| 6,097,994 | * | 8/2000 | Navab et al. ........................ 700/245 |
| 6,098,048 | * | 8/2000 | Dashefsky et al. .................... 705/10 |
| 6,104,384 | * | 8/2000 | Moon et al. ......................... 345/168 |
| 6,124,841 | * | 9/2000 | Aoyama ............................... 345/127 |
| 6,128,097 | * | 10/2000 | Parker et al. ......................... 358/1.2 |

* cited by examiner

*Primary Examiner*—Richard Hjerpe
*Assistant Examiner*—Kimnhung Nguyen
(74) *Attorney, Agent, or Firm*—Michael Best & Friedrich LLP

(57) ABSTRACT

An apparatus and method of calibrating a video monitor relative to an external object is claimed. A video representation of an object is displayed on a video monitor. An external object is placed adjacent the monitor. The size of the video representation of the object is changed to substantially match of the size of at least a portion of the external object.

24 Claims, 2 Drawing Sheets

SYSTEM FOR AND METHOD OF CALIBRATING A COMPUTER MONITOR

RELATED APPLICATIONS

This application claims the benefit under 37 C.F.R. §119 of prior filed, co-pending Provisional Application No. 60/072,248, filed on Jan. 22, 1998.

BACKGROUND OF THE INVENTION

The invention relates to a method and apparatus for calibrating a video monitor relative to an external object. More particularly, the present invention relates to a method and apparatus for calibrating any video monitor such that the size of an object displayed on the calibrated video monitor will be the same regardless of monitor size and resolution.

Video monitors generate images on a cathode ray tube (CRT) or liquid crystal display (LCD) by energizing one or more pixels on the CRT or LCD to generate light visible to the user of the monitor. A line, for example, is represented by illuminating a series of adjacent pixels. Pixels are the fundamental building blocks from which all computer graphics are created. A pixel is the smallest possible dot that can be represented on a given video monitor. All pixels on a given monitor are the same size. However, pixel size varies from monitor to monitor.

When displaying to scale the image of an object having a known size, on a given monitor, it is necessary to divide the horizontal and vertical size of the object by a scale factor that is specific to the given monitor. This scale factor is related to the pixel size.

When displaying physiological patient waveforms, e.g., electrocardiogram (ECG) or blood pressure (BP), it is standard to use a vertical scale of 10 millivolts (mV)/millimeter (mm), and a horizontal scale of 25 mm/second (sec.).

If a pixel on a given monitor is known to have a height (vertical) and width (horizontal) of 0.20833 millimeters (mm), the pixel height in a vertical direction of a 1 millivolt (mV) ECG signal, using a vertical scale of 10 mm/mV, is calculated by the following equation:

height of signal=(1 mV×10 mm/mV)/0.20833 mm/pixel height of signal=48 pixels

Similarly, the pixel width in a horizontal direction (as a function of time) of a 1 mV ECG signal at a scan rate of 25 millimeters per second is calculated by the following equation:

width of signal/time=(25 mm/sec)/(0.20833 mm/pixel)

width of signal/time=120 pixels/sec

SUMMARY OF THE INVENTION

Prior art patient monitoring systems used standardized video monitors so that the scale and scale factor of the systems are fixed. This allows the calculations necessary to accurately display an image of a given size to be programmed into the software of the system.

Present day video display monitors range greatly in size and in pixel resolution. For example, displays on notebook computers have pixel resolutions such as 640×480. Larger 21" monitors have pixel resolutions such as to 1280×1024. Further, the size of an individual pixel is dependant not only on the dimensions of the screen, but also the resolution of the monitor. For example, a 17" or 21" monitor may both have a pixel resolution of 1280×1024, but the actual pixel sizes may be different.

The various sizes available in video monitors, and the various pixel sizes on those monitors, pose a unique problem in designing medical waveform display devices—namely, determining the size that waveforms should be represented on display devices. Displaying some waveforms, such as blood pressure waveforms, is straightforward. Sample values are scaled proportionally between two arbitrary coordinates on the video display. Points are chosen based on available screen area. As more waveforms are added to the display, the vertical area dedicated to a given waveform is reduced, and thus the amplitude of the waveform is proportionally decreased. The horizontal area dedicated to a given waveform is fixed at a rate of 25 millimeters per second.

Electrocardiograph (ECG) waveforms, however, are subject to an industry standard for gain and time base as specified by the Association for the Advancement of Medical Instrumentation (AAMI). The display of an ECG waveform is to be the same size, regardless of the type, size, or pixel resolution of the display monitor used. The AAMI specification is most concerned with aspect ratio (i.e., gain/time). The aspect ratio is derived from a standard value of 10 mm/mV for gain and 25 mm/sec for time. This results in an aspect ratio of 0.4 sec/mV.

Accordingly, the invention provides a method and apparatus to display a waveform such that the size of the waveform remains the same regardless of the type of monitor used to display the waveform. Specifically, the invention allows a user to easily communicate the pixel and screen size of the monitor to the computer thereby allowing the computer to accurately calculate the number of pixels to energize and the rate at which the pixels should be energized in order to accurately display an image to a given scale.

The method of the present invention calibrates a video monitor relative to an external object, such as a ruler. A video representation of an object (a "video" ruler) is displayed on the video monitor. The user then places an external object (a "real" ruler) on the surface of the video monitor. The user changes the size of the "video" ruler to substantially match the size of the "real" ruler.

The invention also provides an apparatus for calibrating a video monitor relative to an external object. The apparatus includes a video monitor for presenting a video display, and means for calibrating the video display relative to a reference external to the monitor.

It is an advantage of the invention to provide a method and apparatus of calibrating a video monitor relative to an external object regardless of the size or resolution of the monitor.

It is another advantage of the invention to display an image on the video monitor, wherein the image has the same size (relative to a scale) regardless of the display monitor being used.

Other features and advantages of the invention are set forth in the following drawings, detailed description and claims.

Figure 1:
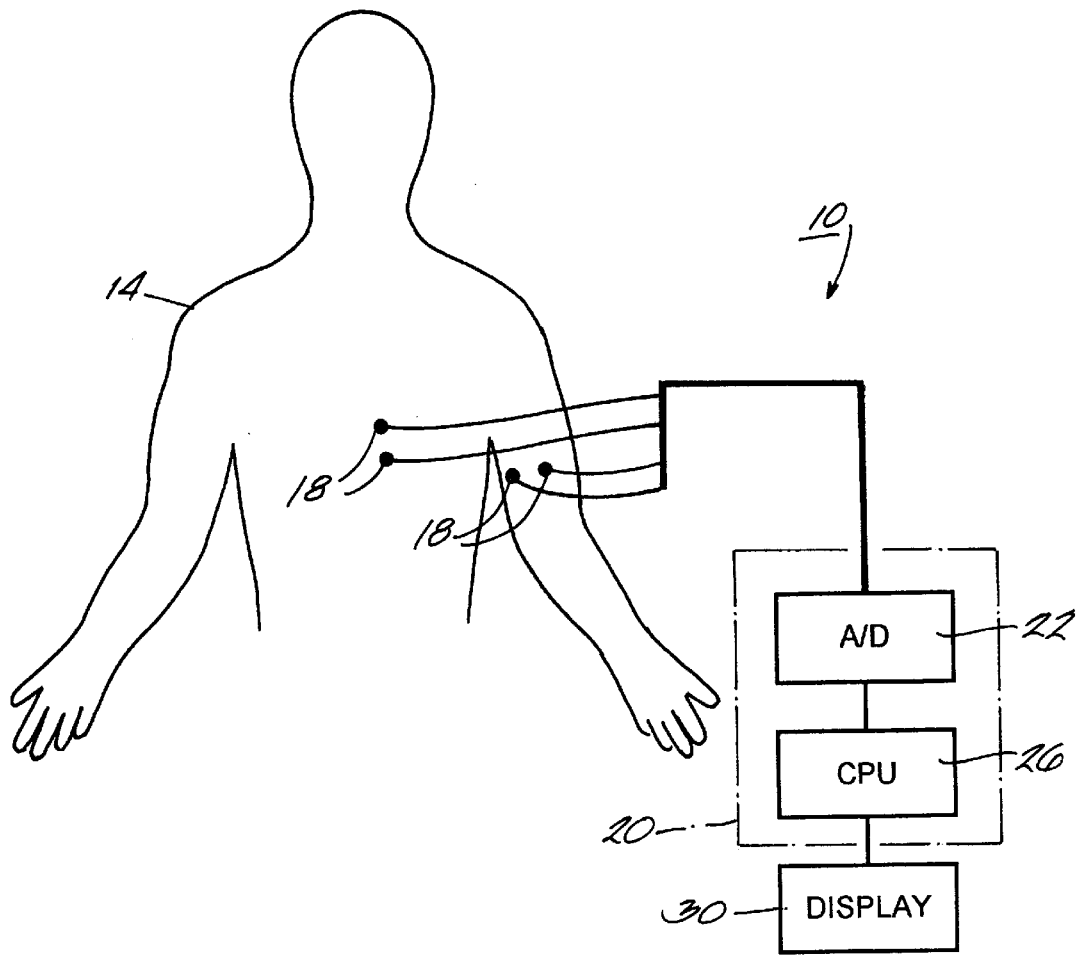
FIG. 1 is a block diagram illustrating a patient monitoring system according to the invention.

Before one embodiment of the invention is explained in detail, it is to be understood that the invention is not limited in its application to the details of the construction and the arrangements of the components set forth in the following description or illustrated in the drawings. The invention is capable of other embodiments and are carried out in various ways. Also, it is to be understood that the phraseology and terminology used herein is for the purpose of description and should not be regarded as limiting.

DETAILED DESCRIPTION OF THE PREFERRED EMBODIMENT(S)

FIG. 1 illustrates the patient monitoring system 10 of the invention. The patient monitoring system 10 acquires and displays physiological patient data. While the monitoring system 10 can be used in connection with monitoring any kind of physiological parameter, in the preferred embodiment, the monitoring system 10 is for monitoring a patient's electrical cardiac activity and blood pressure. Monitoring system 10 is coupled to the patient 14 by an array of sensors or transducers which may include, for example, electrodes 18 mounted on the patient's chest and arm for electrocardiogram testing. Hereinafter, the term "sensor" and "transducer" will be used synonymously, and each term will be defined as including the subject matter of the other term.

The patient monitoring system 10 includes a computer 20 connected to the sensors 18, and a video display monitor 30 connected to the computer. The computer includes an analog-to-digital converter (A/D) 22 and a central processing unit (CPU) 26. The signals derived from the sensors are converted from analog form to digital form by A/D 22 and provided to the CPU 26. CPU 26 prepares the data for display on the display monitor 30.

The display monitor 30 is a conventional computer-style display monitor having a generally rectangular cathode ray tube (CRT). The size of the display screen of the display monitor will vary (as will the resolution and pixel size), depending upon the type of display monitor. The vertical location of the pixels is defined by a y-coordinate and the horizontal location of the pixels is defined by an x-coordinate. As is known in the art, each pixel is capable of being energized electronically so that the pixel emits light visible to the user of the monitoring system.

Figure 2:
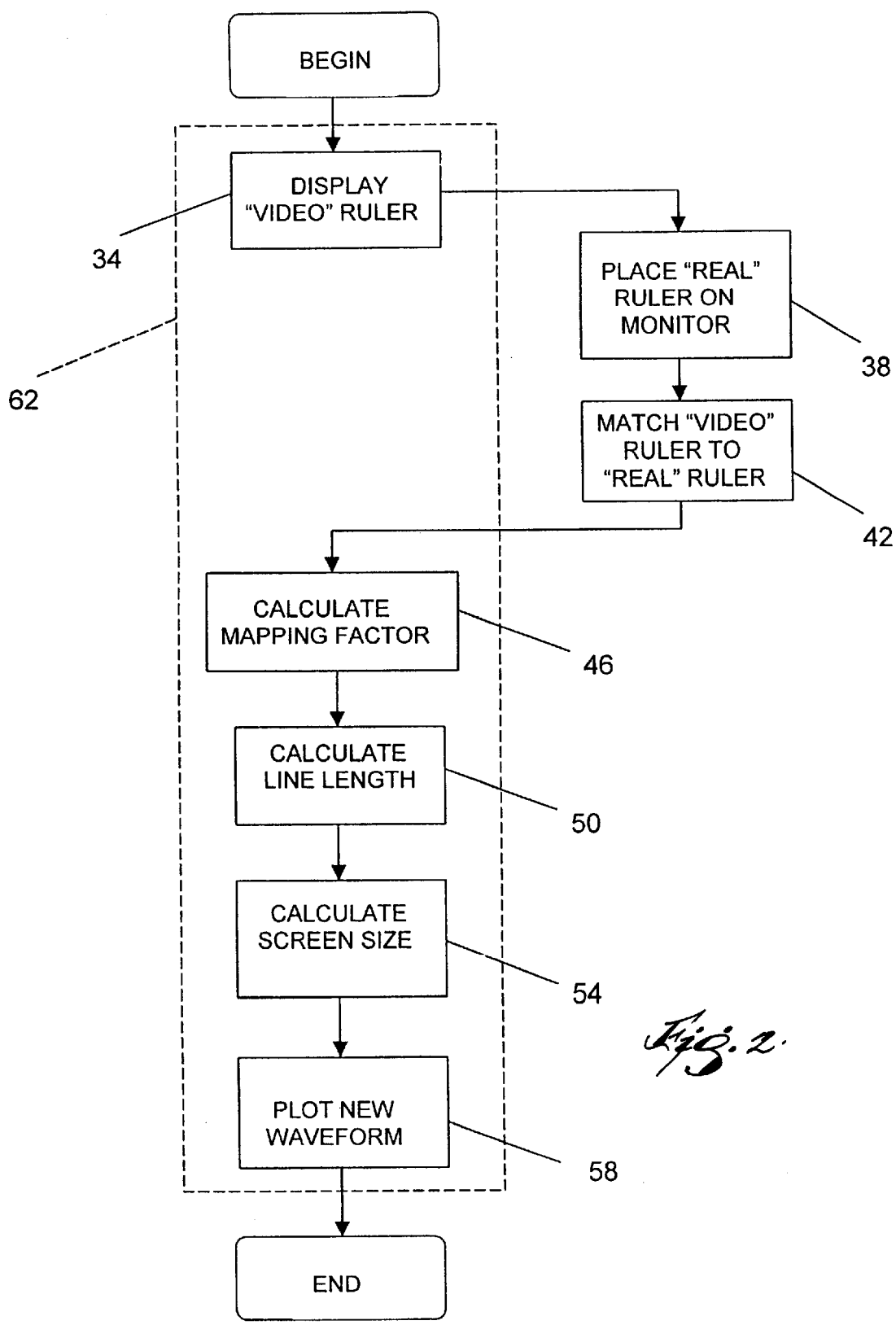
FIG. 2 is a flowchart illustrating the method of the invention.

FIG. 2 is a flowchart illustrating operation of the patient monitoring system 10 embodying the invention, and the use of the method in connection with the patient monitoring system 10. Box 62 indicates functions that are preferably performed by CPU 26, while acts 38 and 42 require human intervention. The functions of box 62 are preferably effected using software operatively associated with computer 20. The software may be run on the computer 20 in the same way that it is commonly known to run other software packages, including storing the software on the computer hard drive (not shown) or random access memory (not shown); running the software from a CDROM drive, disk drive, or tape drive (none of which are shown); or accessing the software from a network (also not shown). The software provides a means for calibrating the video representation of an object relative to a reference external to the monitor.

A video ruler (34) is depicted on the display 30. In a preferred embodiment, two video rulers are presented on the display 30—a horizontal video ruler and a vertical video ruler. The ruler(s) are provided with graduation marks. The video ruler is preprogrammed to indicate the number of pixels per unit length of the video ruler. A user then places a "real ruler" (38) onto the display 30 such that either the horizontal or vertical video ruler is aligned with the real ruler at the zero point.

The video ruler is then matched with the real ruler (42). In one embodiment, the CPU displays a movable reference icon controlled by user initiated movement of a "mouse" across a mouse pad. By dragging the "mouse" across the pad, the reference icon is moved across the display. The act of matching the video ruler to the real ruler includes moving the reference icon to a point on the video ruler corresponding to a length measurement, "clicking" or "engaging" the mouse, and dragging the mouse (either left or right for the horizontal ruler, or up or down for the vertical ruler) so that the graduation marks on the video ruler expand or contract in coincidence with the mouse movement until the size of the video ruler and the real ruler substantially match. The mouse or mouse button is then released or disengaged. In other embodiments, other display or cursor-manipulating devices may be used, such as a track-ball, a stylus, or a touch screen system.

Upon matching of the real and video rulers, pixel size is determined in both the horizontal and vertical directions. By taking the total pixel length of the ruler and dividing it by the real measurement length of the ruler, a mapping factor of pixels per millimeter is determined for both the horizontal and vertical directions. Separate horizontal and vertical mapping factors are calculated, as a pixel may have a different width and length. The mapping factor (46) is determined by the following equation:

$$MF_{pix/mm} = L_{pix}/(L_{unit}*SC), \text{ where}$$

MF=Mapping factor

L=Length

SC=Standard conversion value to convert from units being used on the screen (inches or centimeters) to millimeters From the mapping factor, the total screen size is calculated (54). Total screen size is determined from the following equations:

$$\text{Screen Size}_{HORZ} = RES_{(HORZ)pix}/MF_H$$

$$\text{Screen Size}_{VERT} = RES_{(VERT)pix}/MF_V$$

Total screen size is preferably stored in a configuration file so that the mapping factor is recalculated each time the system is restarted. It is preferable to store values for screen size because the screen size remains constant regardless of the resolution. The mapping factor, however, does not remain constant in that the mapping factor is based on the resolution, which may be changed by the user. Thus, each time the system is restarted, the mapping factor is recalculated by:

$$MF_V = RES_{(VERT)pix}/\text{Screen Size}_{VERT}$$

$$MF_H = RES_{(HORZ)PIX}/\text{Screen size}_{HORZ}$$

Once the screen size and the mapping factor are determined, an ECG waveform is plotted (58) on the display to the AAMI standard specification. In plotting the waveform, the line length (in number of pixels) in horizontal and vertical directions is established by the following two equations:

$$H_{pix} = 1/S_{HZ}*25 \text{ mm/sec } MF*_{HORZ}$$

$$V_{pix} = P_{mV}*10 \text{ mm/sec*}MF_{VERT}, \text{ where}$$

H=number of pixels per sample in a horizontal direction,

S=sample rate of data,

V=number of pixels in a vertical direction based on the magnitude of the data point, P=value of current data point, $MF_{HORZ}$ and $MF_{VERT}$=horizontal and vertical mapping factors determined from calibration, 25 mm/sec=the standard for time base, and 10 mm/mV=the standard for gain In one embodiment, an aspect ratio is maintained. The aspect ratio is a ratio of the screen size and is not particular to ECG waveforms. By maintaining an aspect ratio, adjusting one ruler (i.e., either the horizontal or vertical ruler) will automatically cause the other ruler (i.e., either the horizontal or vertical ruler) to adjust in such a manner as to keep the aspect ratio constant. In a preferred embodiment, the aspect ratio is set to be 1.333 (4:3) which, in many cases, represents square pixels and satisfies the AAMI specification. In another embodiment, the aspect ratio is customized by the user.

Various features and advantages of the invention are set forth in the following claims.

What is claimed is:

1. A method of calibrating a video monitor relative to an external object, the method comprising:

displaying a video representation of an object on the video monitor;

placing the external object adjacent the monitor; and changing the size of the video representation of the object to substantially match the size of at least a portion of the object.

2. A method as set forth in claim 1, wherein the act of changing the size of the video representation of the object further comprises generating a cursor and positioning the cursor on the video representation of the object such that at least a portion of the video representation of the object and at least a portion of the external object are substantially the same size.

3. A method as set forth in claim 2, wherein the act of positioning the cursor utilizes a mouse.

4. A method as set forth in claim 2, wherein the act of positioning the cursor utilizes a track ball.

5. A method as set forth in claim 2, wherein the act of positioning the cursor utilizes a stylus pen.

6. A method as set forth in claim 2, wherein the act of positioning the cursor utilizes a touch screen system.

7. A method as set forth in claim 1, and further comprising determining a mapping factor based on the size of the video representation of the object, and determining total screen size of the monitor based on the mapping factor.

8. A method as set forth in claim 7, wherein the mapping factor is a ratio of a number of pixels per millimeter.

9. A method as set forth in claim 1, wherein the external object is a ruler.

10. A method as set forth in claim 1, wherein the video representation of an object is a video representation of a ruler.

11. A method as set forth in claim 1, wherein the act of changing the size of the video representation of the object to match the size of at least a portion of the external object includes the act of determining the pixel size for the monitor.

12. A method as set forth in claim 1, wherein the act of changing the size of the video representation of the object includes changing the horizontal size of the video representation of the object, thereby automatically changing the vertical size of the video representation of the object.

13. A method as set forth in claim 1, wherein the act of changing the size of the video representation of the object includes changing the vertical size of the video representation of the object, thereby automatically changing the horizontal size of the video representation of the object.

14. A method as set forth in claim 1, wherein the act of changing the size of the video representation of the object includes the act of maintaining an aspect ratio.

15. A method as set forth in claim 14, wherein the aspect ratio is 4:3.

16. An apparatus comprising:

a video monitor for presenting a video representation of an object;

a computer connected to the monitor; and software associated with the computer to calibrate the video monitor relative to a reference object adjacent to and external to the monitor.

17. The apparatus as set forth in claim 16, wherein the reference external to the monitor is a ruler.

18. The apparatus as set forth in claim 16, wherein the video representation of the object is a video representation of a ruler.

19. The apparatus as set forth in claim 16, wherein the computer displays a cursor on the monitor, and wherein the position of the cursor on the video representation of the object causes the software to alter the video representation of the object such that at least a portion of the video representation of the object and at least a portion of the external object are substantially the same size.

20. An apparatus comprising:

a video monitor for presenting a video representation of an object;

means for calibrating the video monitor relative to a reference object adjacent to and external to the monitor.

21. The apparatus as set forth in claim 20, wherein the reference external to the monitor is a ruler.

22. The apparatus as set forth in claim 20, wherein the video representation of the object is a video representation of a ruler.

23. The apparatus as set forth in claim 20, wherein the means for calibrating further displays a cursor on the monitor, and wherein the position of the cursor on the video representation of the object causes the software to alter the video representation of the object such that at least a portion of the video representation of the object and at least a portion of the external object are substantially the same size.

24. A method as set forth in claim 1, wherein the video representation of an object on the video monitor is a video representation of the external object adjacent the monitor.

* * * * *